US012740811B2

(12) United States Patent
Karnezis

(10) Patent No.: US 12,740,811 B2
(45) Date of Patent: Sep. 22, 2026

(54) SPINAL ANCHORING ELEMENT SYSTEM

(71) Applicant: CONCEPT SPINE LTD, Salfords (GB)

(72) Inventor: Ioannis Karnezis, Salfords (GB)

(73) Assignee: CONCEPT SPINE LTD, Salfords (GB)

( * ) Notice: Subject to any disclaimer, the term of this patent is extended or adjusted under 35 U.S.C. 154(b) by 77 days.

(21) Appl. No.: 18/551,980

(22) PCT Filed: Feb. 2, 2022

(86) PCT No.: PCT/IB2022/050910
§ 371 (c)(1),
(2) Date: Sep. 22, 2023

(87) PCT Pub. No.: WO2022/200870
PCT Pub. Date: Sep. 29, 2022

(65) Prior Publication Data

US 2024/0164813 A1 May 23, 2024

(30) Foreign Application Priority Data

Mar. 24, 2021 (GB) ..................................... 2104126

(51) Int. Cl.
*A61B 17/70* (2006.01)
*A61B 17/17* (2006.01)
*A61B 17/00* (2006.01)

(52) U.S. Cl.
CPC ...... *A61B 17/7005* (2013.01); *A61B 17/1757* (2013.01); *A61B 17/7011* (2013.01);
(Continued)

(58) Field of Classification Search
CPC ............ A61B 17/7005; A61B 17/1757; A61B 17/7011
See application file for complete search history.

(56) References Cited

U.S. PATENT DOCUMENTS 5,306,275 A 4/1994 Bryan
2003/0236447 A1 12/2003 Ritland
(Continued)

FOREIGN PATENT DOCUMENTS

GB 2605162 B 5/2023
JP 2020509832 A 4/2020
(Continued)

OTHER PUBLICATIONS

Japanese Patent Office, Notice of Reasons for Refusal of Japanese Application No. 2023-558771 (Jul. 1, 2025).
(Continued)

*Primary Examiner* — Ellen C Hammond
(74) *Attorney, Agent, or Firm* — Ware, Fressola, Maguire & Barber LLP

(57) ABSTRACT

It is known to use pedicle screws and connectors to treat deformities in a spinal column. However, there are cases when screws must be installed in certain positions relative to each other as otherwise the connector may not fit correctly between them. A spinal anchoring element system is therefore provided, comprising a guide tool 60 for aligning a screw-path forming instrument 90 for use in forming a screw-path in a vertebra 10 for the subsequent installation of a pedicle screw 20, the guide tool comprising a guide tool stem 80 and a screw-path forming instrument receiving section 70, the guide tool stem and the screw-path forming instrument receiving section being immovable relative to one another.

13 Claims, 16 Drawing Sheets

(52) U.S. Cl.
CPC ................. *A61B 2017/0092* (2013.01); *A61B 2017/00982* (2013.01)

(56) References Cited

U.S. PATENT DOCUMENTS

| | | | | |
|---|---|---|---|---|
| 2004/0204710 | A1 | 10/2004 | Patel et al. | |
| 2006/0036242 | A1 | 2/2006 | Nilsson et al. | |
| 2006/0122607 | A1 | 6/2006 | Kolb | |
| 2006/0265074 | A1* | 11/2006 | Krishna | A61B 17/7064 606/279 |
| 2010/0331897 | A1* | 12/2010 | Lindner | A61B 17/7041 606/305 |
| 2011/0034258 | A1 | 2/2011 | Abdelgany | |
| 2016/0338738 | A1 | 11/2016 | Karnezis | |
| 2017/0095270 | A9 | 4/2017 | Karnezis | |
| 2020/0046382 | A1 | 2/2020 | Won | |

FOREIGN PATENT DOCUMENTS

| | | | |
|---|---|---|---|
| WO | 9511632 | A1 | 5/1995 |
| WO | 2007014119 | A2 | 2/2007 |
| WO | 2007035326 | A2 | 3/2007 |
| WO | 2010067113 | A1 | 6/2010 |

OTHER PUBLICATIONS

Combined Search and Examination Report, Application No. GB2104126.4, mailed Aug. 10, 2021 (8 pages).

Examination Report, Application No. GB2104126.4, mailed Jan. 12, 2022 (3 pages).

Examination Report, Application No. GB2104126.4, mailed Jan. 26, 2023 (3 pages).

International Search Report, Application No. PCT/IB2022/050910, mailed May 10, 2022 (4 pages).

Korean IPO, Office Action for Korean Patent Appl. No. 10-2023-7035223 with English translation (Jun. 17, 2026).

* cited by examiner

SPINAL ANCHORING ELEMENT SYSTEM

The present invention relates generally to a spinal anchoring element system, and a method of installing a pedicle screw and finds particular, although not exclusive, utility in spinal column deformity correction surgery through the use of devices which are surgically implantable.

At present, spinal anchoring elements such as pedicle screws are inserted surgically to the posterior elements (pedicles) of the spine as means of mechanical support to the spine in cases of spinal fractures or as a means of correcting the shape of the spine in cases of surgical correction of spinal deformities such as scoliosis.

Multiple pedicle screws may firstly be inserted at various vertebrae of the spine and these pedicle screws may be subsequently connected together. Such connection between two or more implanted pedicle screws is achieved in either a rigid manner, where movement between the connected pedicle screws is prevented or in a movable manner where various desirable degrees of movement between the connected pedicle screws is permitted. Example of connections in a rigid manner has been described in US2011034258A1 which discloses a method for attaching a pedicle screw head to a bone fixator component for securing the bone fixator component in a bone in a polyaxial manner. When such connection between two or more implanted pedicle screws is achieved in a rigid manner the pedicle screws may be connected together by means of connector of the rod type such as disclosed in US2006036242A1. It is known that when the connector is of the rod type the surgeon is commonly required to bend the rod connector in various ways at the time of surgery to achieve a connector shape appropriate for connecting two or more pedicle screws placed at various positions along the spine.

However, the connector may be of a type more complex than a rod and such a connector may not be amenable to bending at the time of surgery in order to achieve a connector shape appropriate for connecting two or more pedicle screws. Such a complex type of a connector is common in cases when the connection between two or more implanted pedicle screws is achieved in a movable manner where various desirable degrees of movement between the connected pedicle screws is permitted. Examples of connections in a movable manner have been described in cases of artificial facet joint prostheses such as in US20060265074A1.

Previous devices for correcting spinal deformities have involved the fixation of bone screws which connect to rods via pivoting connections, for example as described in WO2007014119A2. Also, the use of ratchet mechanisms with spinal implants are known from WO2010067113A1 and US2016338738A1.

In US2016338738A1, connectors are described which may be used to link together individual pedicle screws and allow controlled movement of the pedicle screws in the sagittal plane to thereby correct spinal deformities over time.

The connectors comprise a stem and a pedicle screw receiving section, and a ratchet which controls movement of the stem relative to the pedicle screw receiving section. The pedicle screws comprise a shaft having a screw thread, and a connector stem receiving section. The connector stem receiving section may comprise a ball and socket joint permitting limited articulation of the connector stem relative to the shaft of the pedicle screw.

In this way, relative movement between a series of pedicle screws and connectors is achievable thus providing for an environment whereby spinal deformities are correctable over time.

In order to use a connector to connect two adjacent pedicle screws, the screws must be installed in certain locations as otherwise the connector may not fit correctly between them. This means that during surgery, placement of a pedicle screw is possible only in a limited number of positions, within a specific range, relative to an adjacent pedicle screw. If an adjacent pedicle screw is installed in a position whereby a connector cannot be used to connect them together, or when they are connected together does not provide the required movement limitation to the spinal column, the pedicle screw would need to be moved. This, of course, is undesirable. Rather, it is important to install pedicle screws in their correct positions on the first attempt.

Moreover, pedicle screws are typically installed after a path has been created in the vertebra. These paths are created using a tool such as a screw-path forming instrument which is then removed after the path has been formed. If a connector, connected to a first installed pedicle screw, is used to guide the screw-path forming instrument, then the connector may become scratched or otherwise damaged. It is undesirable to use scratched or damaged connectors as these may cause tissue damage after surgery.

Accordingly, it is desirable to provide tools to allow for the correct and accurate positioning of pedicle screws during such surgery to avoid screw misplacement, to avoid the subsequent inability to connect the screws together using connectors, and to avoid damage to the connectors.

In a first aspect, the invention provides a spinal anchoring element system comprising a guide tool for aligning a screw-path forming instrument for use in forming a screw-path in a vertebra for the subsequent installation of a pedicle screw, the guide tool comprising a guide tool stem and a screw-path forming instrument receiving section, the guide tool stem and the screw-path forming instrument receiving section being immovable relative to one another.

In use, after a first pedicle screw has been installed in a vertebra, the guide tool may be connected to the first pedicle screw, by insertion of the guide tool stem into the guide tool stem receiving section of the pedicel screw. The screw-path forming instrument receiving section may be then used to receive one or more screw-path forming instruments to create a screw-path in an adjacent vertebra. The screw-path forming instrument may then be removed. The guide tool may also then be removed. A second pedicle screw may then be installed into the screw-path with a connector which is connected to the first and second pedicle screws.

The guide tool may comprise substantially radiolucent material. This is so that during surgery the precise position and orientation of the screw-path for the screw may be optimally chosen by use of radiography because the screw-path forming tools (which are not radiolucent) are not obscured by the guide tool.

By contrast if a non-radiolucent connector is used, instead of the guide tool, during surgery to act as a guide for preparation of the screw-path for the screw, the nonradiolucent connector may obscure the radiographic image of the elements of the spine. This leads to a risk that the screw-path for the screw may not be formed in the optimal location and/or not with the optimum direction. This may lead to damage of important structures of the spine, such as the nerves or the spinal cord. If the guide tool is radiolucent then this problem may be avoided.

The screw-path forming instrument receiving section may comprise a channel open at opposite axial ends, the channel having a bore, wherein the bore has a longitudinal axis.

The channel may be defined by a cylindrical wall, and the wall may include a slot allowing, in use, a guide wire to be inserted into the channel. The guide wire may be used for placement of the pedicle screw. The guide tool stem may be arranged to fit, in use, into a guide tool stem receiving section of an adjacent pedicle screw.

The spinal anchoring element system may further comprise a screw-path forming instrument for use in forming a screw-path in a vertebra for the subsequent installation of a pedicle screw. For example, an awl may be used to create an initial dent or hole in the bone. Then the awl may be replaced with a pedicle finder, both of which may be understood to be screw-path, or hole, forming instruments.

The screw-path forming instrument may include a mating section which may have a size and shape which closely matches that of the bore of the channel (screw-path forming instrument receiving section) so that the mating section is receivable, in use, in the bore of the channel to thereby align the screw-path forming instrument.

The screw-path forming instrument may include a depth limiter to limit axial movement, in one direction, of the screw-path forming instrument parallel to the longitudinal axis of the bore of the channel along said longitudinal axis, with the screw-path forming instrument received in the screw-path forming instrument receiving section. The depth limiter may be a collar arranged on a stem of the screw-path forming instrument.

After the pedicle finder has been employed, to create an initial path for the installation of the pedicle screw, it may be removed from the guide tool.

The spinal anchoring element system may further comprise a screw-path forming instrument receiving member, the screw-path forming instrument receiving member including attachment means for attaching it to the guide tool, the screw-path forming instrument receiving member including an internal screw thread for rotationally receiving a screw-path forming instrument for creating a thread on the inside surface of the screw-path created in the vertebra by the screw-path forming instrument.

The attachment means may be a clamping mechanism which clamps the screw-path forming instrument receiving member to the guide tool.

The spinal anchoring element system may further comprise a screw-path forming instrument, including an external screw thread, for rotational reception in the screw-path forming instrument receiving member, and for creating the thread on the inside surface of the screw-path created in the vertebra by the screw-path forming instrument.

The screw-path forming instrument may comprise a guide tool mating section for aligning the screw-path forming instrument in relation to the guide tool.

The guide tool mating section may have a size and shape which closely matches that of the bore of the channel so that the guide tool mating section is receivable, in use, into the bore of the channel to thereby align the screw-path forming instrument.

In use, the screw-path forming instrument may be inserted into an aperture at an axial end of the screw-path forming instrument receiving member, distal from the guide tool, and then rotated to move towards, by the interaction of the screw threads, into the screw-path previously created in the vertebra to thereby create a thread on the internal surface of the screw-path. In this regard, the screw-path forming instrument may be considered to be a tap. The amount of depth insertion of the screw-path forming instrument into the vertebra may be controlled by rotational movement of the screw-path forming instrument relative to the screw-path forming instrument receiving member.

The guide tool mating section may include a depth limiter to limit axial movement, in one direction, of the screw-path forming instrument parallel to the longitudinal axis of the bore of the channel along said longitudinal axis, with the screw-path forming instrument received in the screw-path forming instrument receiving section of the guide tool. The depth limiter may be a collar on the stem of the screw-path forming instrument which has a radius larger than the bore of the channel such that it cannot enter the channel.

The spinal anchoring element system may further comprise a pedicle screw, the pedicle screw comprising a guide tool stem receiving section for receiving, in use, the guide tool stem of an adjacent guide tool. It is to be noted that the guide tool stem receiving section may also be known as a connector stem receiving section because it may be used to receive the connector stem after a guide tool has been removed.

The spinal anchoring element system may further comprise a connector, the connector comprising a connector stem and a pedicle screw receiving section, the pedicle screw receiving section for receiving, in use, the guide tool stem receiving section of a pedicle screw. The connector stem and pedicle screw receiving section may be movable relative to one another about an axis parallel to the intersection of the coronal and transverse planes, in use.

In use, the guide tool may be removed from the first pedicle screw and replaced with the connector. The connector stem may be inserted into the guide tool stem receiving section of a pedicle screw.

The connector may further comprise a ratchet for controlling movement of the pedicle screw receiving section relative to the connector stem, about an axis parallel to the intersection of the coronal and transverse planes, in use.

The connector stem may have a shape and size substantially the same as the guide tool stem. The shapes and sizes may be identical. In this regard, the guide tool may be selected from a range of guide tools, each having a different stem length. Furthermore, the connector may be selected from a range of connectors, each having a different connector stem length. The connectors in the range of connectors may have equivalent shaped and sized connector stems as the guide tool stems in the range of guide tools. The shapes and sizes may be identical. In this way, the surgeon may select a guide tool which has the most appropriately shaped and sized guide tool stem in order to ensure correct connection between adjacent pedicle screws, and then after forming the path for the second pedicle screw, having used the selected guide tool, replace the selected guide tool with the equivalent connector.

The pedicle screw may comprise a shaft having a screw thread, and the guide tool stem receiving section of the pedicle screw may comprise a ball and socket joint for articulation of the guide tool stem relative to the shaft. This may allow for greater choice of relative positions between the various installed components of the system.

In a second aspect, the invention may provide a method of installing a second pedicle screw in a second vertebra adjacent to a first vertebra, the first vertebra including a preinstalled first pedicle screw, the method comprising the steps of:

a) providing a guide tool according to the first aspect;

b) inserting the guide tool stem into the guide tool stem receiving section of the first pedicle screw pre-installed in the first vertebra;
c) positioning the screw-path forming instrument receiving section in a selected location in relation to the second vertebra;
d) inserting the screw-path forming instrument into the screw-path forming instrument receiving section;
e) operating the screw-path forming instrument to thereby create an initial hole in the second vertebra;
f) removing the screw-path forming instrument from the guide tool;
g) attaching a screw-path forming instrument receiving member to the guide tool;
h) inserting another screw-path forming instrument into the screw-path forming instrument receiving section;
i) operating the screw-path forming instrument to thereby create a screw-path comprising a thread on the inside of the screw-path created in the second vertebra;
j) removing the screw-path forming instrument from the screw-path forming instrument receiving member;
k) removing the guide tool stem from the guide tool stem receiving section of the first pedicle screw pre-installed in the first vertebra;
l) replacing the guide tool with a connector, the connector having a connector stem and a pedicle screw receiving section; and
m) inserting the second pedicle screw into the pedicle screw receiving section of the connector and into the threaded screw-path formed in the second vertebra.

In the method of installing a second pedicle screw, the connector in step l) may be selected from a range of connectors, each having a different connector stem length, such that the selected connector has the same stem length as the stem length of the selected guide tool.

In a third aspect, the invention may provide a method of installing a second pedicle screw in a second vertebra adjacent to a first vertebra, the first vertebra including a preinstalled first pedicle screw, the method comprising the steps of:

a) providing a guide tool according to the first aspect;
b) inserting the guide tool stem into the guide tool stem receiving section of the first pedicle screw pre-installed in the first vertebra;
c) positioning the screw-path forming instrument receiving section in a selected location in relation to the second vertebra;
d) inserting the screw-path forming instrument into the screw-path forming instrument receiving section;
e) operating the screw-path forming instrument to thereby create an initial hole in the second vertebra;
f) removing the screw-path forming instrument from the guide tool;
g) removing the guide tool stem from the guide tool stem receiving section of the first pedicle screw pre-installed in the first vertebra
h) attaching a screw-path forming instrument receiving member to a connector, the connector having a connector stem and a pedicle screw receiving section;
i) inserting the connector stem into the guide tool receiving section of the first pedicle screw pre-installed in the first vertebra;
j) inserting the screw-path forming instrument into the screw-path forming instrument receiving section;
k) operating the screw-path forming instrument to thereby create a screw-path comprising a thread on the inside of the screw-path created in the second vertebra;
l) removing the screw-path forming instrument from the screw-path forming instrument receiving member;
m) removing the screw-path forming member from the connector; and
n) inserting the second pedicle screw into the pedicle screw receiving section of the connector and into the threaded screw-path formed in the second vertebra.

In this alternative method, instead of attaching the screw-path forming instrument receiving member to the guide tool, the guide tool is removed and replaced with the connector, and the screw-path forming instrument receiving member is attached to that. In this case, the connector stem acts in the same way as the guide tool stem and is immovable relative to the screw-path forming instrument receiving section.

The step of removing the screw-path forming member from the connector in step m) may occur with the connector connected to the first pedicle screw, or after it has been removed from the first pedicle screw.

Due to the screw-path forming member being firmly attached to the connector there is no likelihood of the connector being damaged by the screw-path forming instrument.

In either of the methods of installing a second pedicle screw, the guide tool in step a) may be selected from a range of guide tools, each having a different stem length.

The connector in step h) in the third aspect, may be selected from a range of connectors, each having a different connector stem length, such that the selected connector has the same stem length as the stem length of the selected guide tool.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

Figure 7:
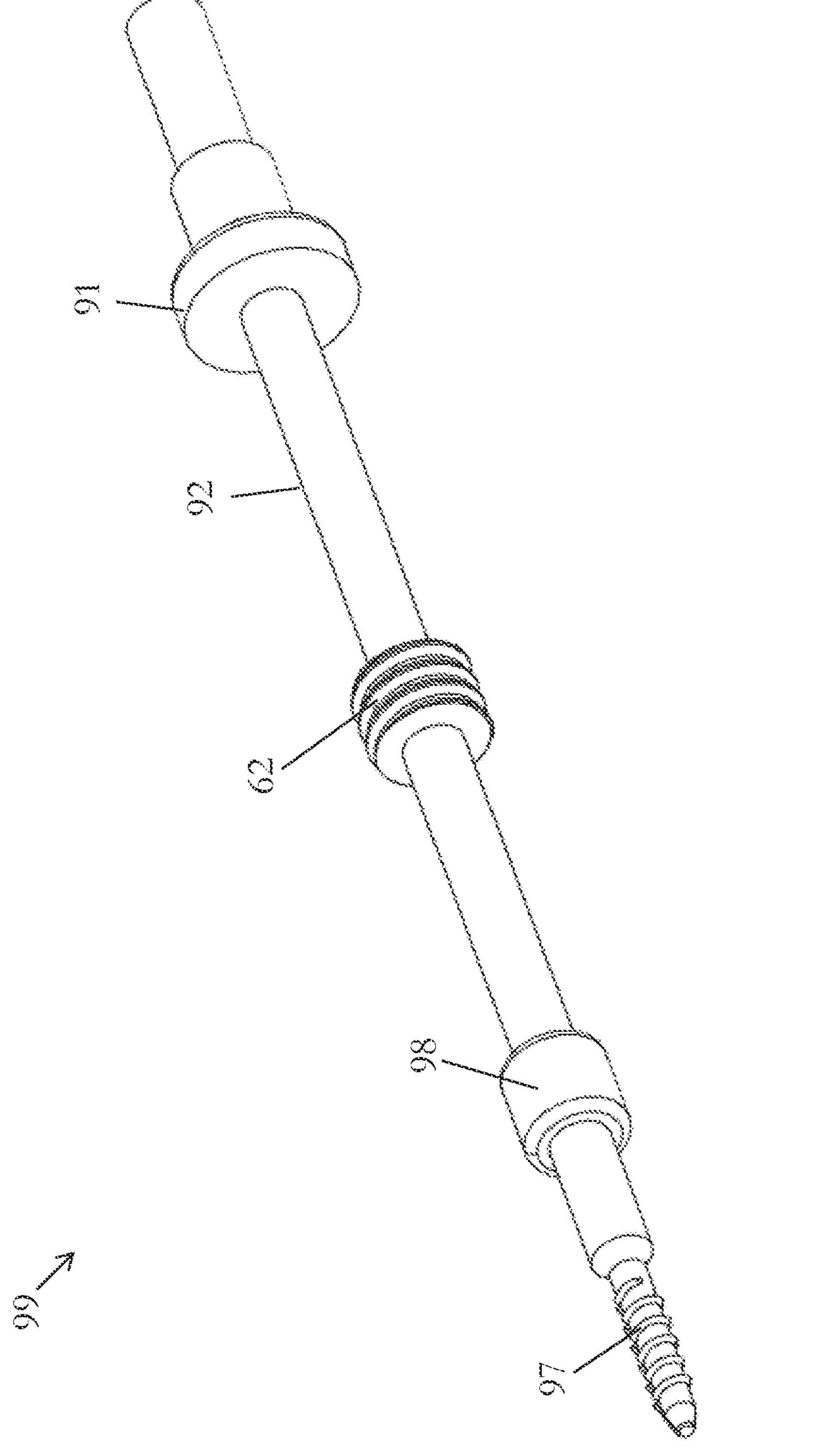
Figure 8:
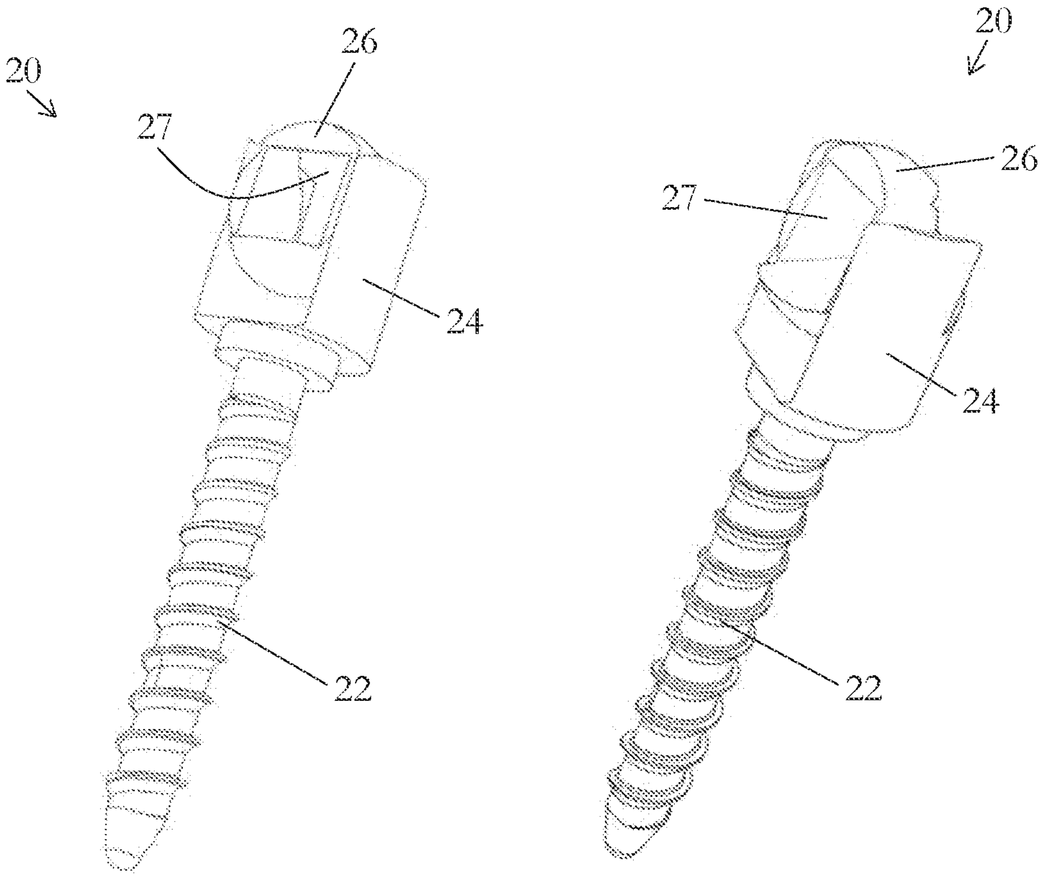
Figure 9:
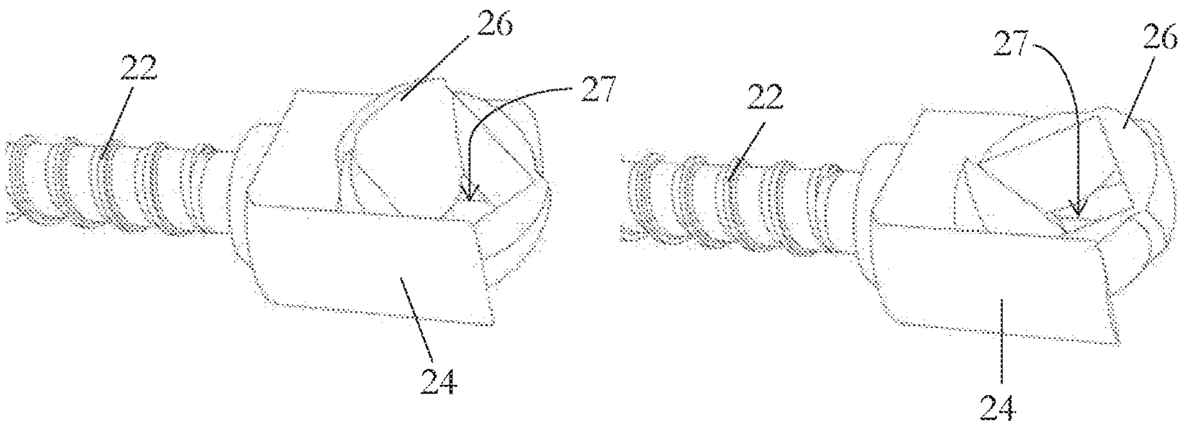
Figure 10:
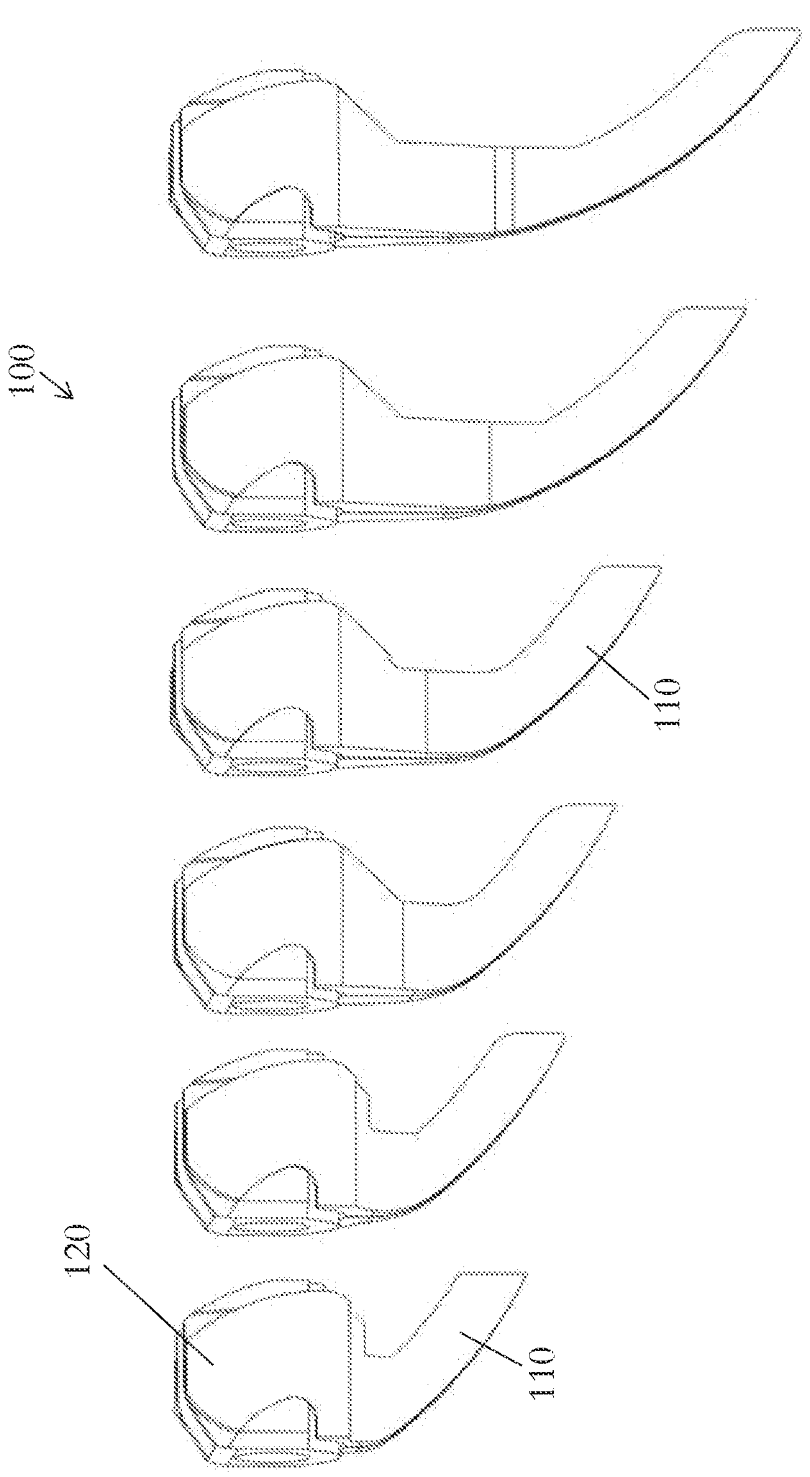
Figure 11:
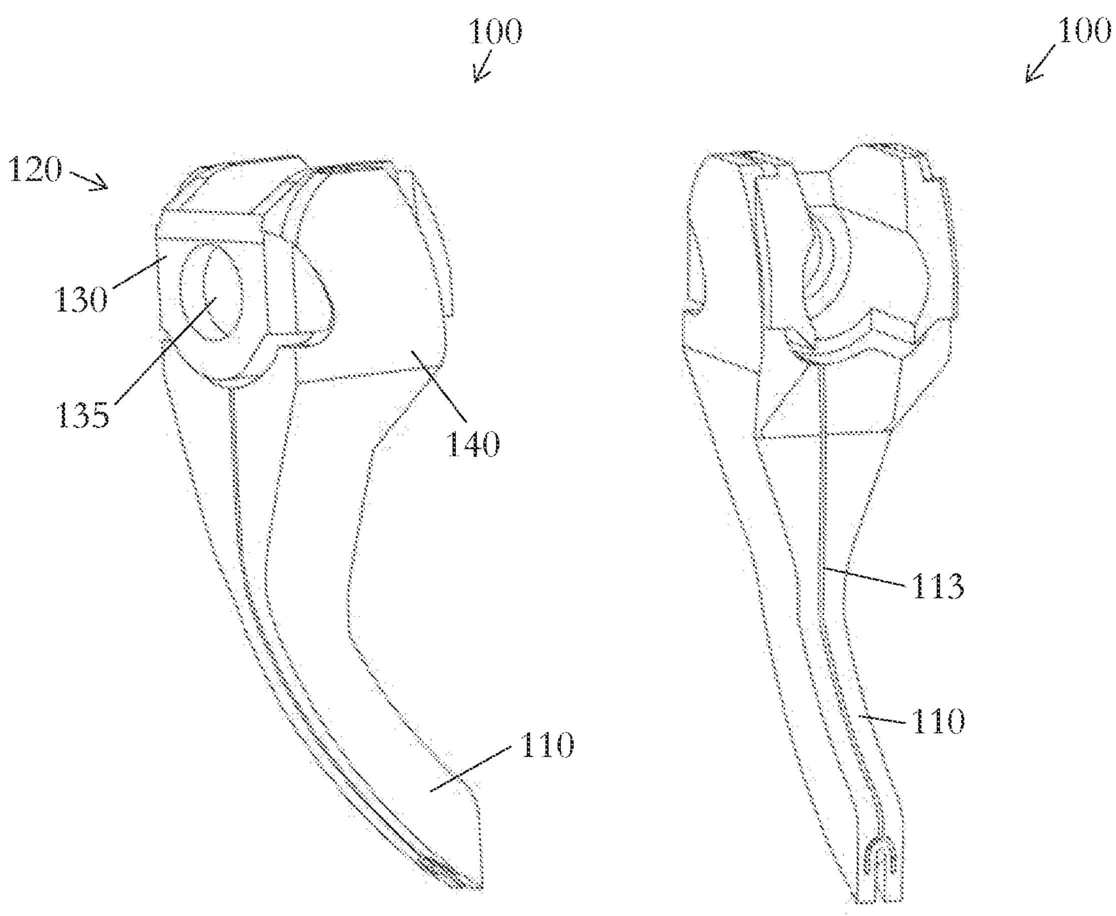
Figure 12:
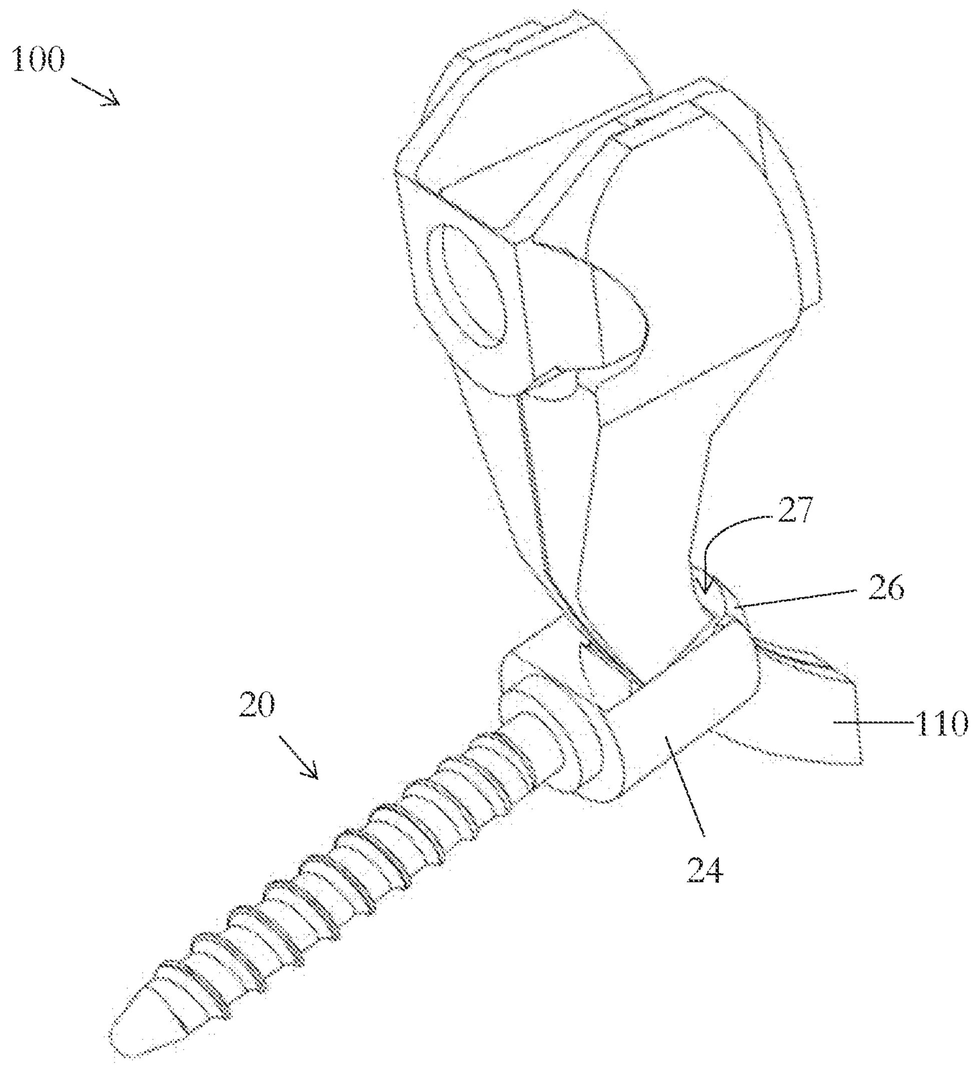
Figure 13:
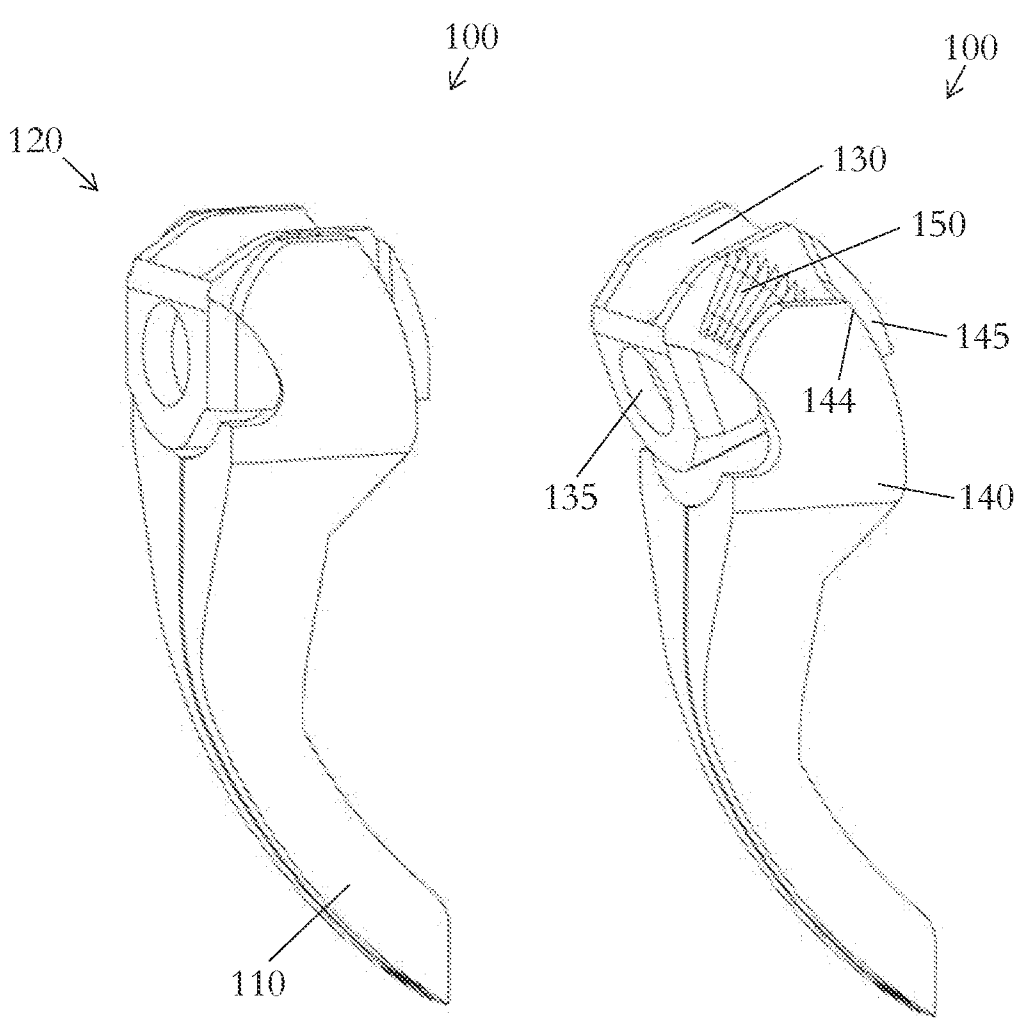

FIG. **6*a*** is a cross-sectional view of a screw-path forming instrument receiving section, and connector attached together;

FIG. **6*b*** is a perspective view of a screw-path forming instrument receiving section, with a portion of a screw-path forming instrument inserted;

FIG. 7 is a perspective view of a screw-path forming instrument;

FIG. 8 is two perspective views of a pedicle screw;

FIG. 9 is two perspective views of portions of a pedicle screw;

FIG. 10 is a perspective view of a range of different sized connectors;

FIG. 11 is two perspective views of a connector;

FIG. 12 is a perspective view of a pedicle screw and a connector;

FIG. 13 is two perspective views of a connector; and

Figure 14:
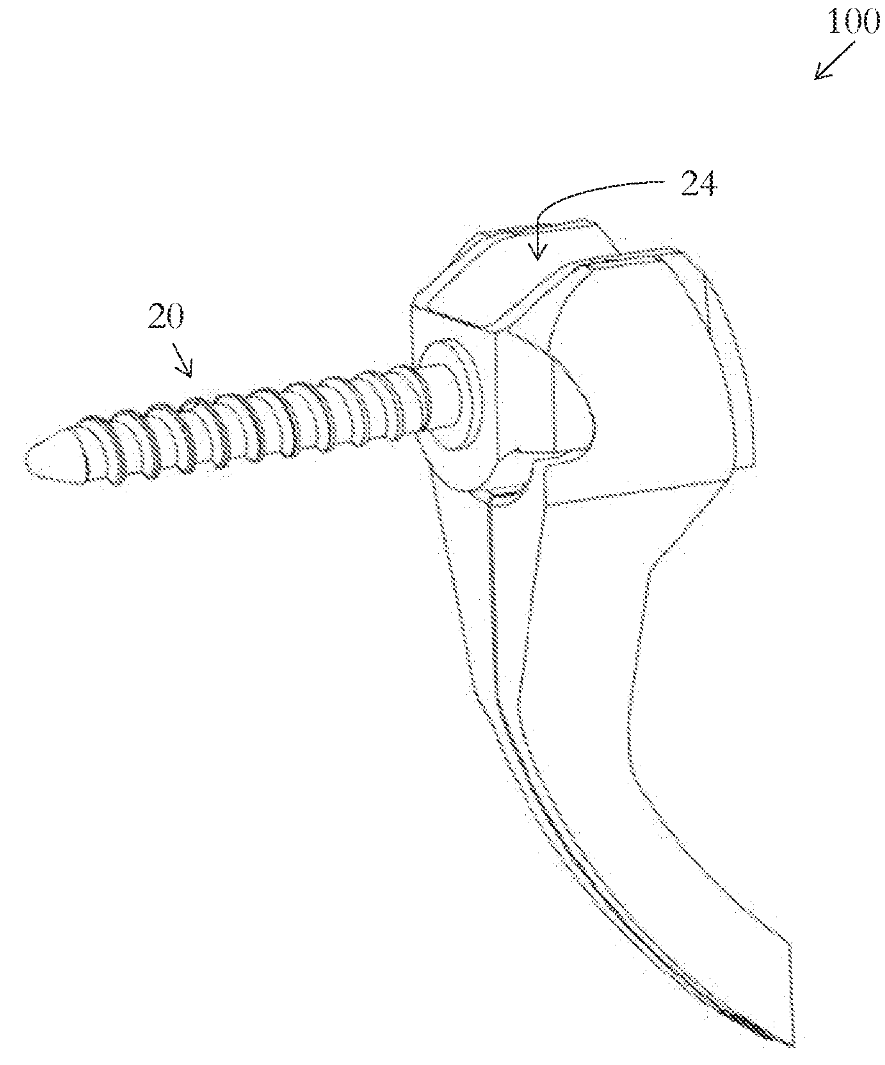

FIG. 14 is a perspective view of a connector and pedicle screw.

The present invention will be described with respect to certain drawings but the invention is not limited thereto but only by the claims. The drawings described are only schematic and are non-limiting. Each drawing may not include all of the features of the invention and therefore should not necessarily be considered to be an embodiment of the invention. In the drawings, the size of some of the elements may be exaggerated and not drawn to scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that operation is capable in other sequences than described or illustrated herein. Likewise, method steps described or claimed in a particular sequence may be understood to operate in a different sequence.

Moreover, the terms top, bottom, over, under and the like in the description and the claims are used for descriptive purposes and not necessarily for describing relative positions. It is to be understood that the terms so used are interchangeable under appropriate circumstances and that operation is capable in other orientations than described or illustrated herein.

It is to be noticed that the term “comprising”, used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression “a device comprising means A and B” should not be limited to devices consisting only of components A and B. It means that with respect to the present invention, the only relevant components of the device are A and B.

Reference throughout this specification to “an embodiment” or “an aspect” means that a particular feature, structure or characteristic described in connection with the embodiment or aspect is included in at least one embodiment or aspect of the present invention. Thus, appearances of the phrases “in one embodiment”, “in an embodiment”, or “in an aspect” in various places throughout this specification are not necessarily all referring to the same embodiment or aspect, but may refer to different embodiments or aspects. Furthermore, the particular features, structures or characteristics of any one embodiment or aspect of the invention may be combined in any suitable manner with any other particular feature, structure or characteristic of another embodiment or aspect of the invention, as would be apparent to one of ordinary skill in the art from this disclosure, in one or more embodiments or aspects.

Similarly, it should be appreciated that in the description various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Moreover, the description of any individual drawing or aspect should not necessarily be considered to be an embodiment of the invention. Rather, as the following claims reflect, inventive aspects lie in fewer than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some features included in other embodiments, combinations of features of different embodiments are meant to be within the scope of the invention, and form yet further embodiments, as will be understood by those skilled in the art. For example, in the following claims, any of the claimed embodiments can be used in any combination.

In the description provided herein, numerous specific details are set forth. However, it is understood that embodiments of the invention may be practised without these specific details. In other instances, well-known methods, structures and techniques have not been shown in detail in order not to obscure an understanding of this description.

In the discussion of the invention, unless stated to the contrary, the disclosure of alternative values for the upper or lower limit of the permitted range of a parameter, coupled with an indication that one of said values is more highly preferred than the other, is to be construed as an implied statement that each intermediate value of said parameter, lying between the more preferred and the less preferred of said alternatives, is itself preferred to said less preferred value and also to each value lying between said less preferred value and said intermediate value.

The use of the term “at least one” may mean only one in certain circumstances. The use of the term “any” may mean “all” and/or “each” in certain circumstances.

The principles of the invention will now be described by a detailed description of at least one drawing relating to exemplary features. It is clear that other arrangements can be configured according to the knowledge of persons skilled in the art without departing from the underlying concept or technical teaching, the invention being limited only by the terms of the appended claims.

Figure 1:
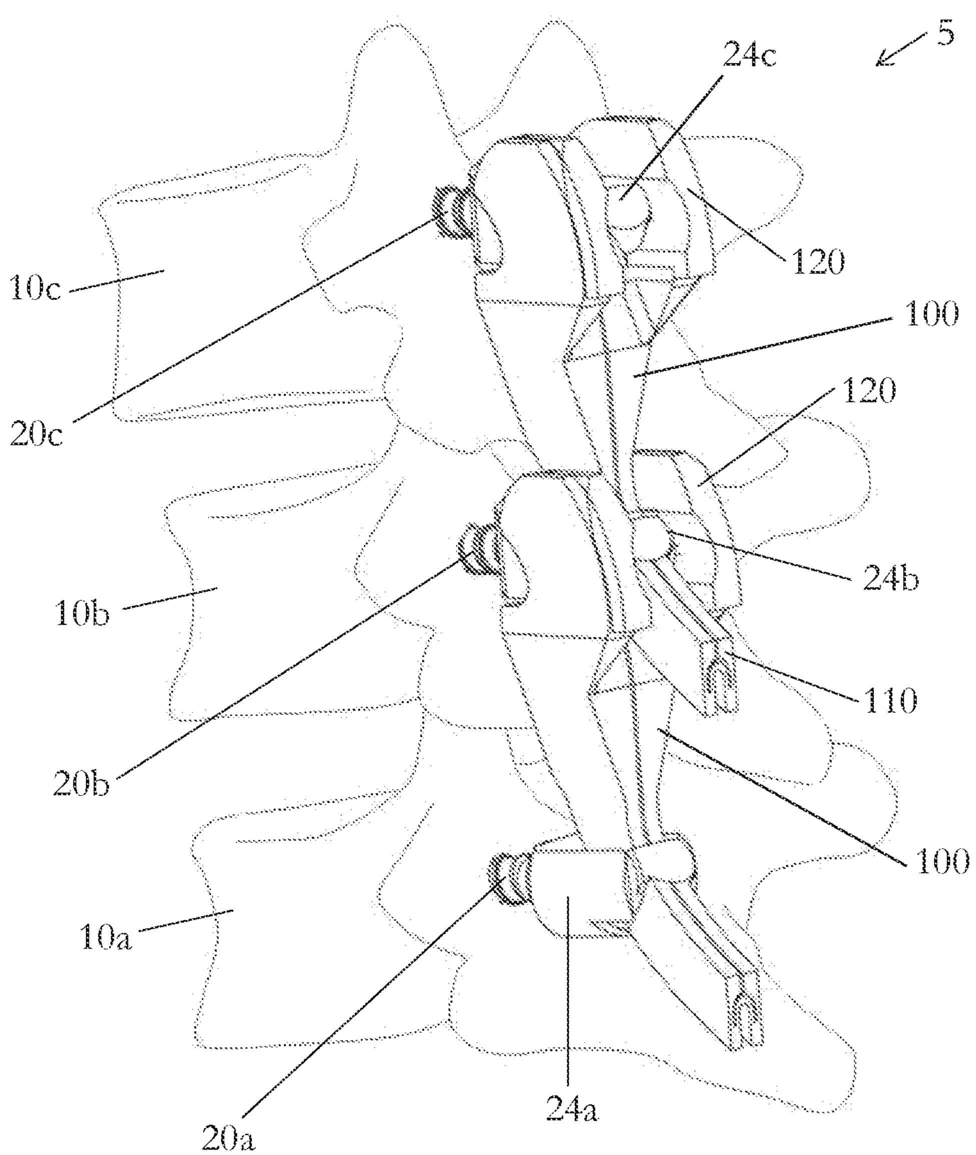
FIG. 1 is a perspective view of three adjacent vertebrae including a spine alignment device.

In [FIG. 1] three adjacent vertebrae 10*a*, 10*b*, 10*c* are shown together with a fitted spinal anchoring element system 5. This device comprises pedicle screws 20*a*, 20*b*, 20*c*, each vertebra including one screw inserted therein to their posterior elements (pedicles). Each pedicle screw includes a connector stem receiving section 24*a*, 24*b*, 24*c*. The uppermost pedicle screw 10*c* has been inserted through a connector 100. The connector 100 comprises a head portion 120 and a stem 110 depending therefrom. The uppermost pedicle screw 10*c* has been inserted through the head portion 120 of the uppermost connector 100. The stem 110 of the uppermost connector extends down and through the connector stem receiving section 24*b* of the middle pedicle screw 20*b*. Likewise, the middle pedicle screw 10*b* has been inserted through a connector 100. The stem 110 of the middle connector extends down and through the connector stem receiving section 24*a* of the lowest pedicle screw 20*a*, the connector stem receiving sections may be sockets.

In this way, the three vertebrae are linked together by the device. The device 5 is arranged to control the relative movement of each vertebra relative to other vertebra. This may be limited to control the relative movement of each vertebra relative to only the adjacent vertebra. The following will explain how the device 5 is installed and its method of use.

Figure 2:
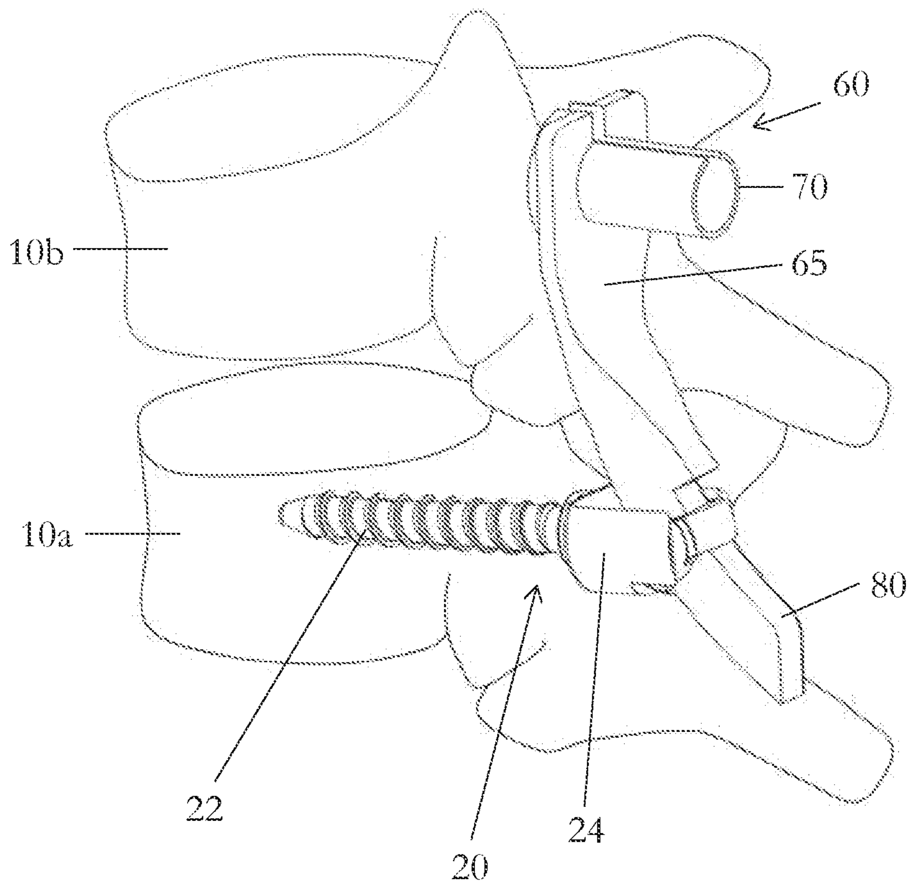
FIG. 2 is a perspective view of two adjacent vertebrae with a pedicle screw and corresponding guide tool.

In [FIG. 2] two adjacent vertebrae 10*a*, 10*b* are shown. The lowest vertebra 10*a* has had a pedicle screw installed into its posterior element (pedicle). The pedicle screw 20 comprises a threaded shaft 22 and a connector stem receiving section 24. However, initially a guide tool 60 is used in place of a connector. The connector 60 comprises a head portion 65 and a stem 80. The stem 80 is received in the connector stem receiving section 24 and as such the connector stem receiving section 24 will be referred to as a guide tool stem receiving section 24 when it is use for this purpose and as a connector stem receiving section 24 when it is used for that purpose.

With the stem 80 received in the guide tool stem receiving section 24 the head portion 65 is located adjacent the uppermost vertebra 10*b*. The guide tool 60 also comprises a channel in the head portion 65 defined by a cylindrical wall (screw-path forming instrument receiving section 70) which extends axially parallel with the longitudinal axis of the installed pedicle screw 20, but in a rearward direction away from the posterior of the vertebra.

Although the pedicle screw 20 is shown as having been installed with the longitudinal axis of the threaded shaft 22 being substantially horizontal, and centrally through the vertebra 10*a*, it is to be understood it may be installed in other directions, especially if the spine has unusual curvature which it is desired to correct.

It is due to the desire to be able to correct spinal aberrations over time that the present invention has been created. As has been described above, in order to use a connector to connect two adjacent pedicle screws, the screws must be installed in certain locations as otherwise the connector may not fit correctly between them. This means that during surgery, placement of a pedicle screw is possible only in a limited number of positions, within a specific range, relative to an adjacent pedicle screw. If an adjacent pedicle screw is installed in a position whereby a connector cannot be used to connect them together, or, when they are connected together, does not provide the required movement limitation to the spinal column, the pedicle screw would need to be moved. This, of course, is undesirable. Rather, it is important to install pedicle screws in their correct positions on the first attempt.

Accordingly, it is desirable to provide tools to allow for the correct and accurate positioning of pedicle screws during such surgery to avoid screw misplacement, to avoid the subsequent inability to connect the screws together using connectors, and to avoid damage to the connectors.

Figure 3:
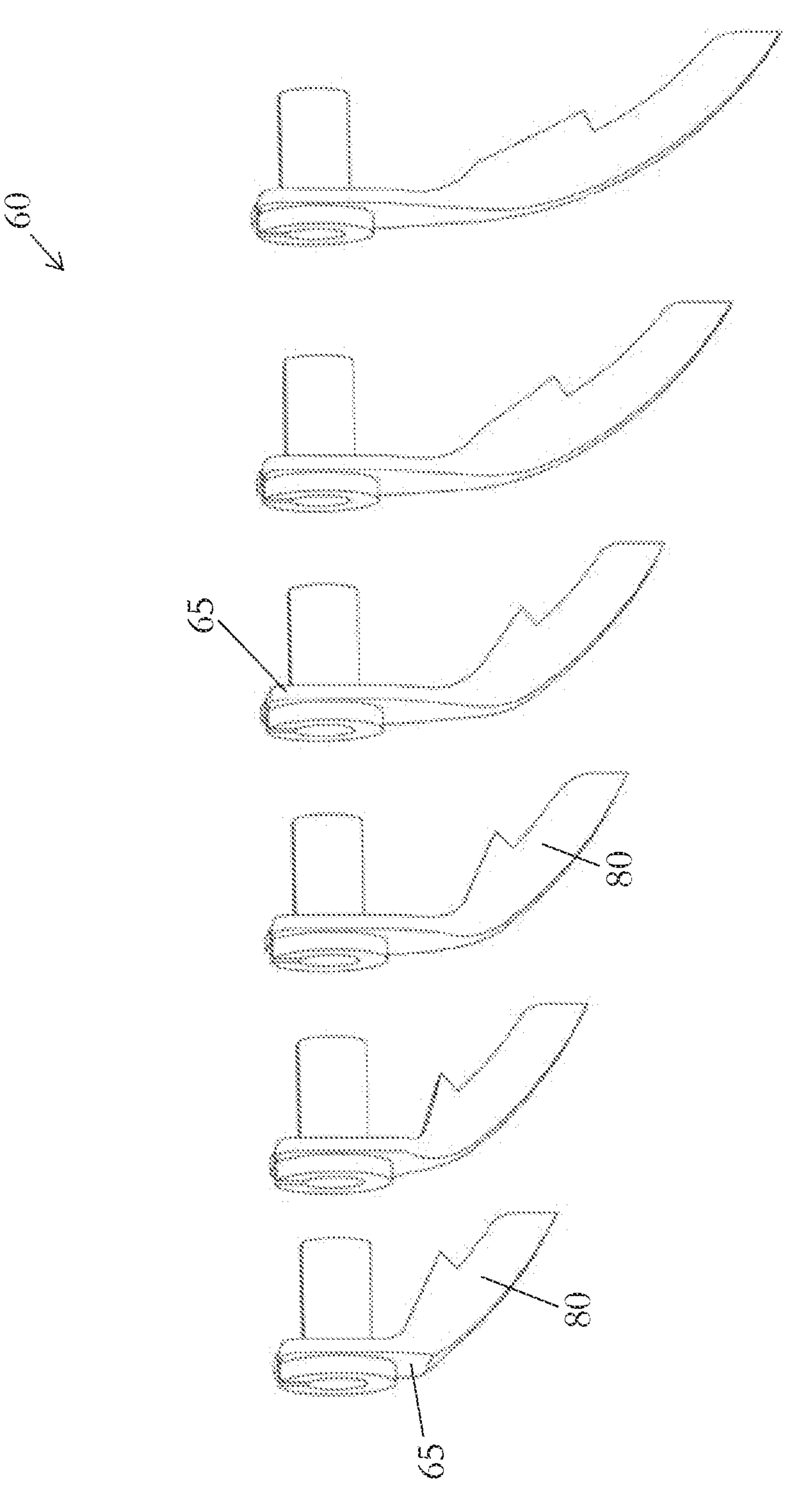
FIG. 3 is a perspective view of a range of different sized guide tools.

This is achieved by use of the guide tool 60, which provides a channel, or screw-path forming instrument receiving section 70 for receiving one or more screw-path forming tools (boring tools) for the creation of a path to receive the next pedicle screw. In use, the surgeon may choose which guide tool 60 to use from a range of guide tools, as shown in [FIG. 3]. Each guide tool 60 has a head portion 65, and a stem 80, but the length of the stem 80 and the angle with which it depends from the head portion 65 is different for each of the guide tools in the range. In this way, the surgeon may choose the most appropriate guide tool from the range to ensure that the screw-path forming instrument receiving section 70 of the chosen guide tool is adjacent the part of the vertebra in which the next pedicle screw is to be installed, and has the longitudinal axis of its bore lying at the most appropriate angle thereto such that the pedicle screw 20 may be installed with the longitudinal axis of its threaded portion 22 lying at an appropriate angle relative to the vertebra.

Figure 4:
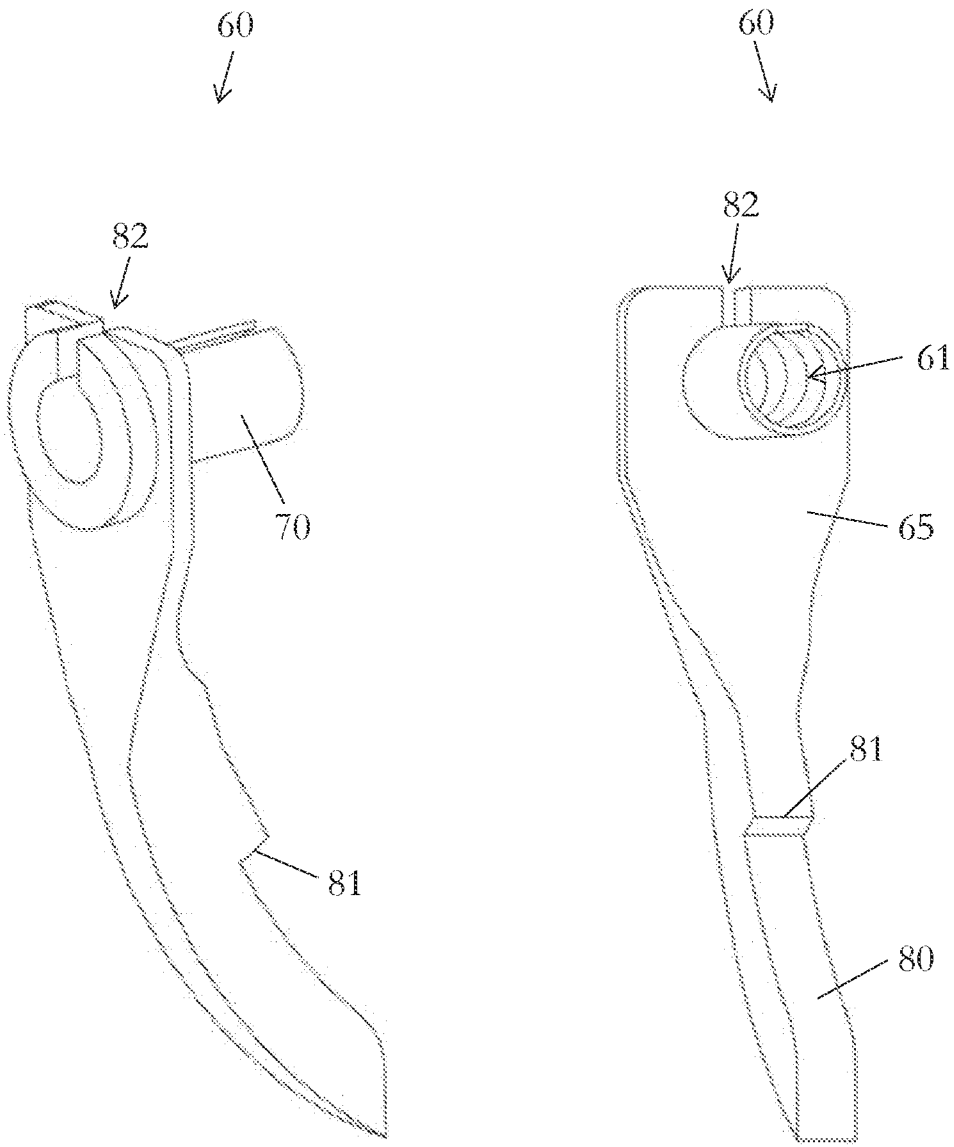
FIG. 4 is two perspective views of a guide tool.

FIG. 4 shows two views of one of the guide tools 60. A slot 82 may be observed passing through the head portion 65 and extending axially along the upper surface of the cylindrical screw-path forming instrument receiving section 70. In use, this slot 82 allows a guide wire to be inserted into the channel 70. Such a guide wire may pass, in use, through and along a central bore of the pedicle screw 20. Each stem 80 includes a step portion 81 which may be used to limit the depth of insertion of the stem 80 into and through the guide tool stem receiving section of the pedicle screw. This limitation is achieved by the step portion widening the upper part of the stem 80, approximately half way along its length between its distal end and the end proximate the head portion 65, such that it is too wide to fit through the guide tool stem receiving section 24 of the pedicle screw 20.

Screw threads 61 are visible on the inside surface of the channel 70. These are optionally present. If they are present, then they may cooperate with the screw threads 62 which may be optionally provided on the external surface of the shaft 92 of the screw-path forming tool (tap) 99 ([FIG. 7]) so as to controllably (by relative rotation thereof) insert the tool 99 into, and remove from, the bone.

Figure 5:
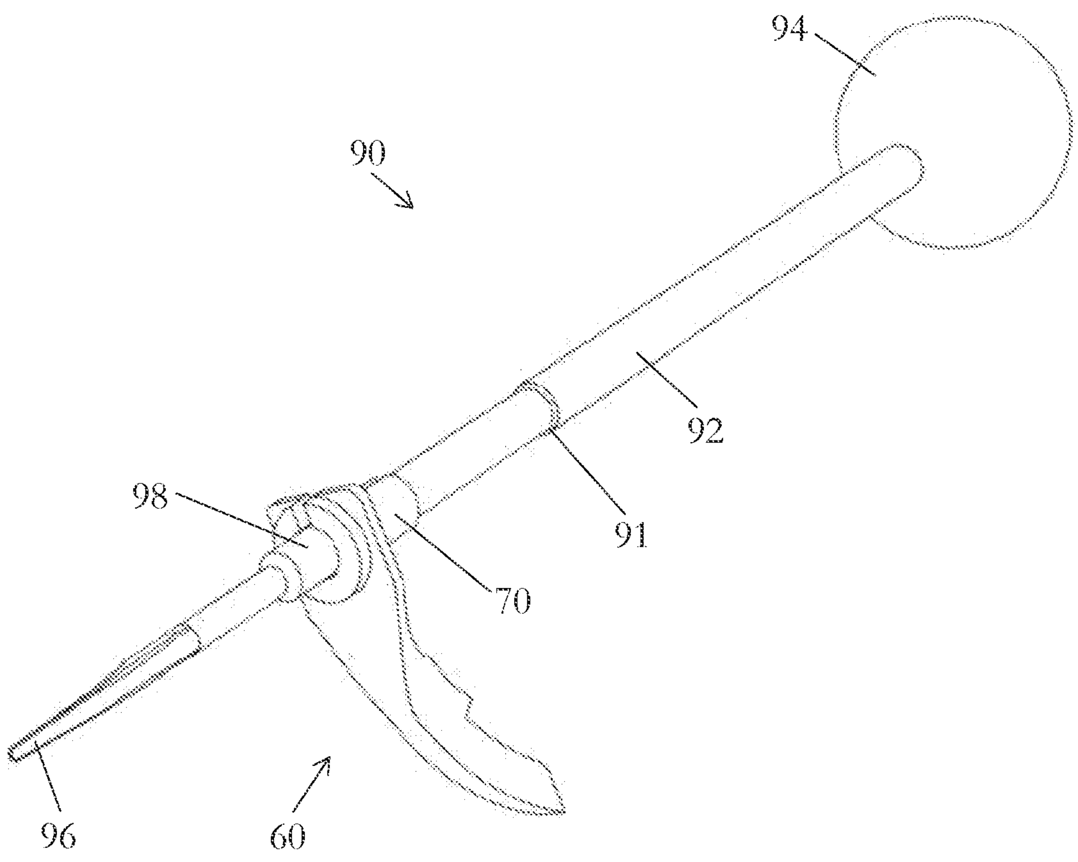
FIG. 5 is a perspective view of a screw-path making tool, and guide tool.

An example of a screw-path forming tool 90 is shown in [FIG. 5], and can be seen to have an elongate shaft 92, with a handle 94 at one end and a relatively sharp point 96, in the form of an awl, at the opposite end. On the shaft is arranged a guide tool mating section 98 which is a cylindrical portion having an outside diameter substantially the same as the inside diameter of the screw-path forming instrument receiving section 70 on the guide tool 60.

The tool 90 is shown in combination with a guide tool 60, with the shaft 92 having been inserted through the channel (screw-path forming instrument receiving section) 70. As the diameter of the guide tool mating section 98 is substantially the same as the inside diameter of the channel of the screw-path forming instrument receiving section 70 the longitudinal axis of the shaft 92 and the longitudinal axis of the channel (screw-path forming instrument receiving section) 70 of the guide tool 60 are co-axial. This allows the surgeon to stably create a screw-path in the vertebra at the chosen position and orientation as dictated by the choice of guide tool and its position relative to the vertebra.

A step 91 is arranged on the length of the shaft 92 to prevent over-insertion of the awl through the guide tool and into the vertebra. The step change increases the diameter of the shaft such that it is greater than the inside diameter of the screw-path forming instrument receiving section 70 such that the it will not pass through the screw-path forming instrument receiving section 70.

Various screw-path forming tools (not all shown) may be used in sequence via the guide tool screw-path forming instrument receiving section 70, such as an awl, followed by a pedicle finder, followed by a tap, as explained below. After an initial hole has been formed in the vertebra, the screw-path forming tool may be removed from the guide tool 60.

A screw-path forming instrument receiving member 30 may now be attached to the guide tool 60. This may be effected either with the guide tool 60 in place with its stem inserted into the pedicle screw below, or after having been removed from the pedicle screw. If the latter, the after attachment of the screw-path forming instrument receiving member 30 to the guide tool 60, the guide tool stem may be reinserted into the pedicle screw below.

Figure 6:
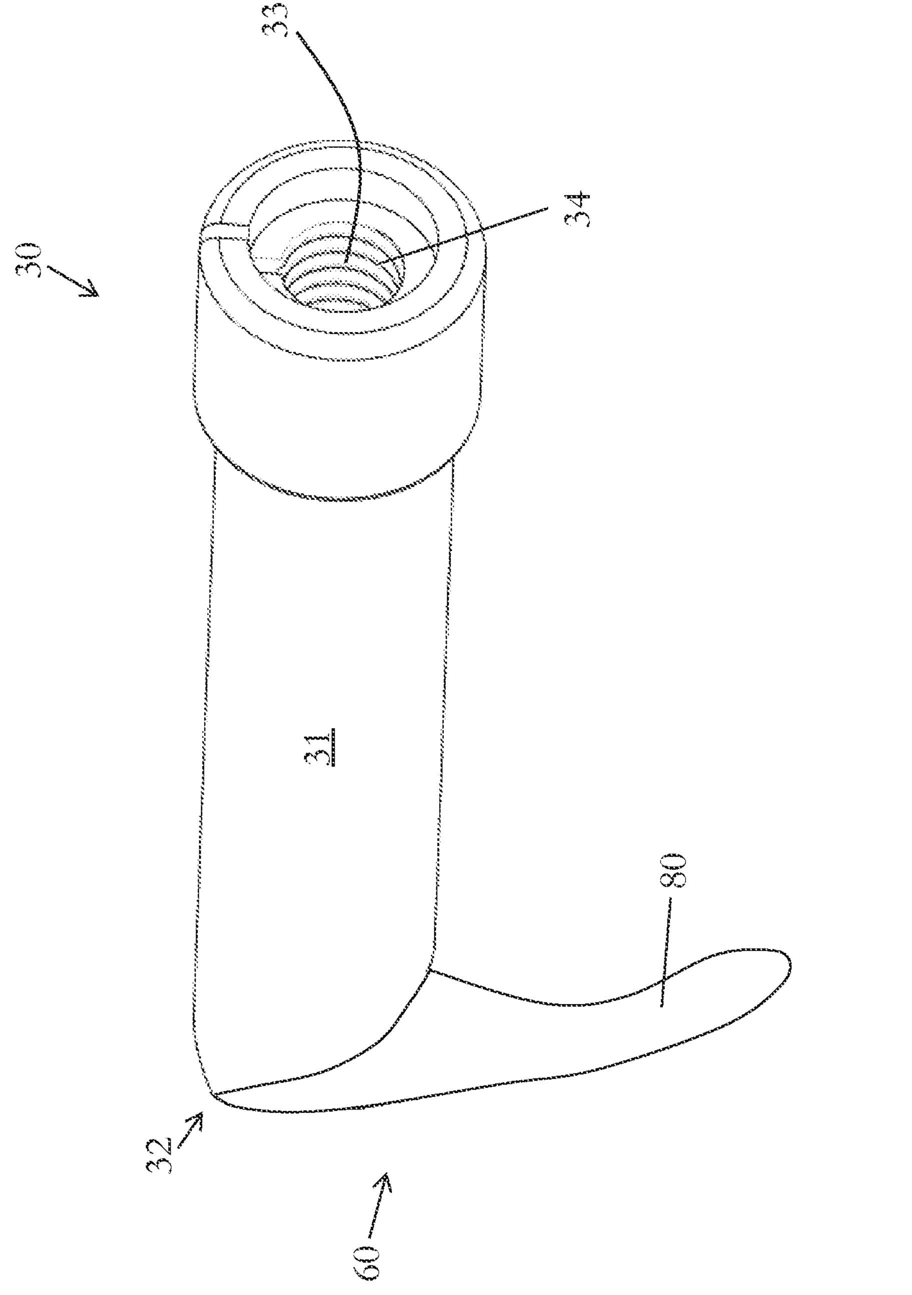
FIG. 6 is a perspective view of a screw-path forming instrument receiving section, and guide tool attached together.

With regard to [FIG. 6], the screw-path forming instrument receiving member 30 comprises a cylindrical body 31 having a bore running along its entire length such that it is hollow. One end of the bore is visible to the right of the body 31 in the form of an opening 33. The screw-path forming instrument receiving member 30 is shown attached to the guide tool 60 at the left-hand end 32. The wall of the bore has threads 34 as will be explained below.

Figure 6A:
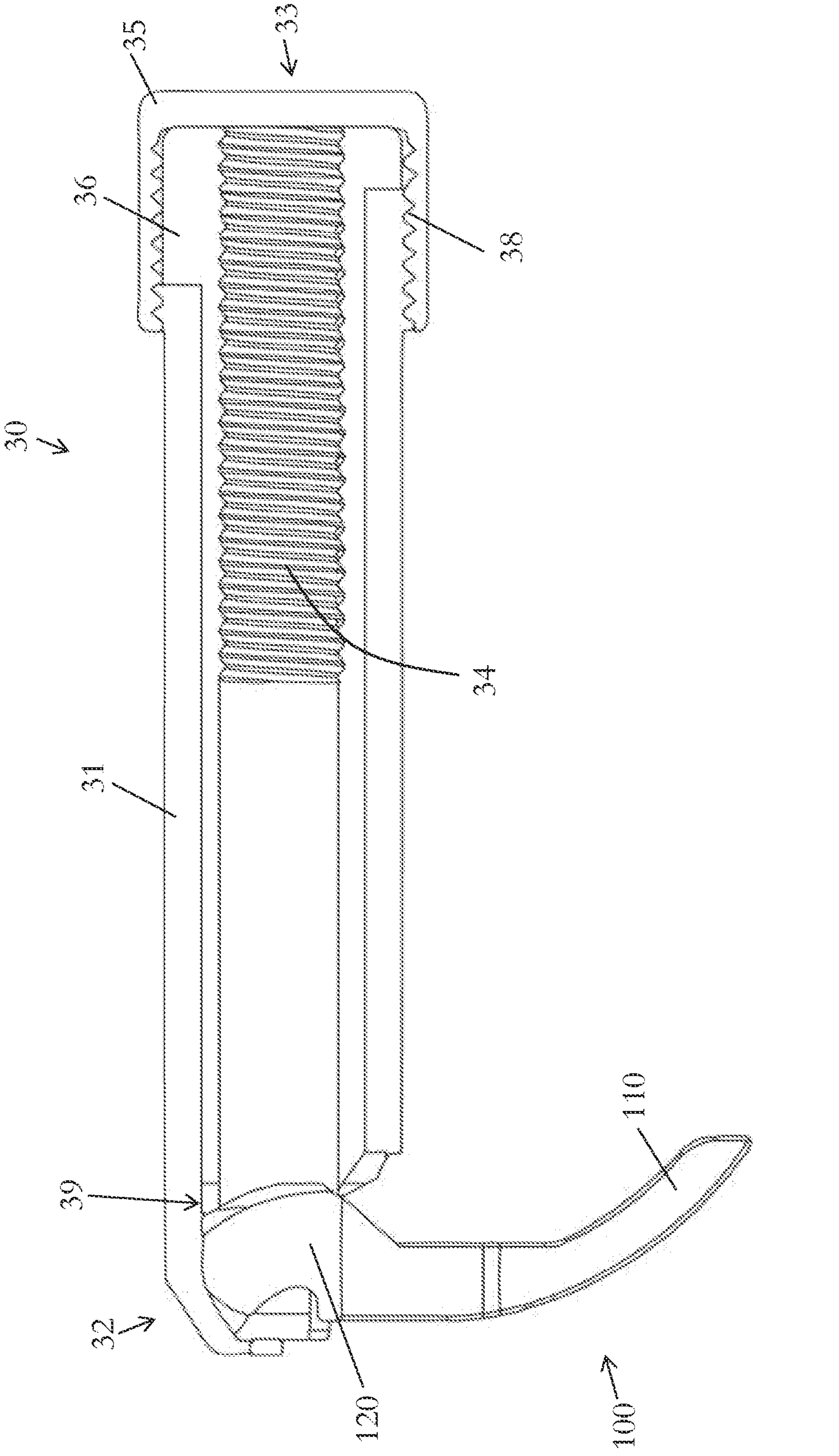

In [FIG. 6*a*], an alternative method is depicted wherein instead of the screw-path forming instrument receiving member 30 being attached to a guide tool 60, it is attached to a connector 100. The screw-path forming instrument receiving member 30 includes an end cap 35 rotatably attached, via co-operating screw threads 38, to the body 31. Within the bore of the body 31 an inner member 36 is slidingly arranged. By rotation of the end cap 35 the inner member 36 is urged towards the end 32 proximate, in use, to the vertebra. This movement of the inner member may be used to clamp the head 120 of the connector 100 between the inner member and the proximate end 32.

The inner threads 34 are shown through with which the threads 62 ([FIG. 7]) of the screw-path forming instrument may engage.

Figure 6B:
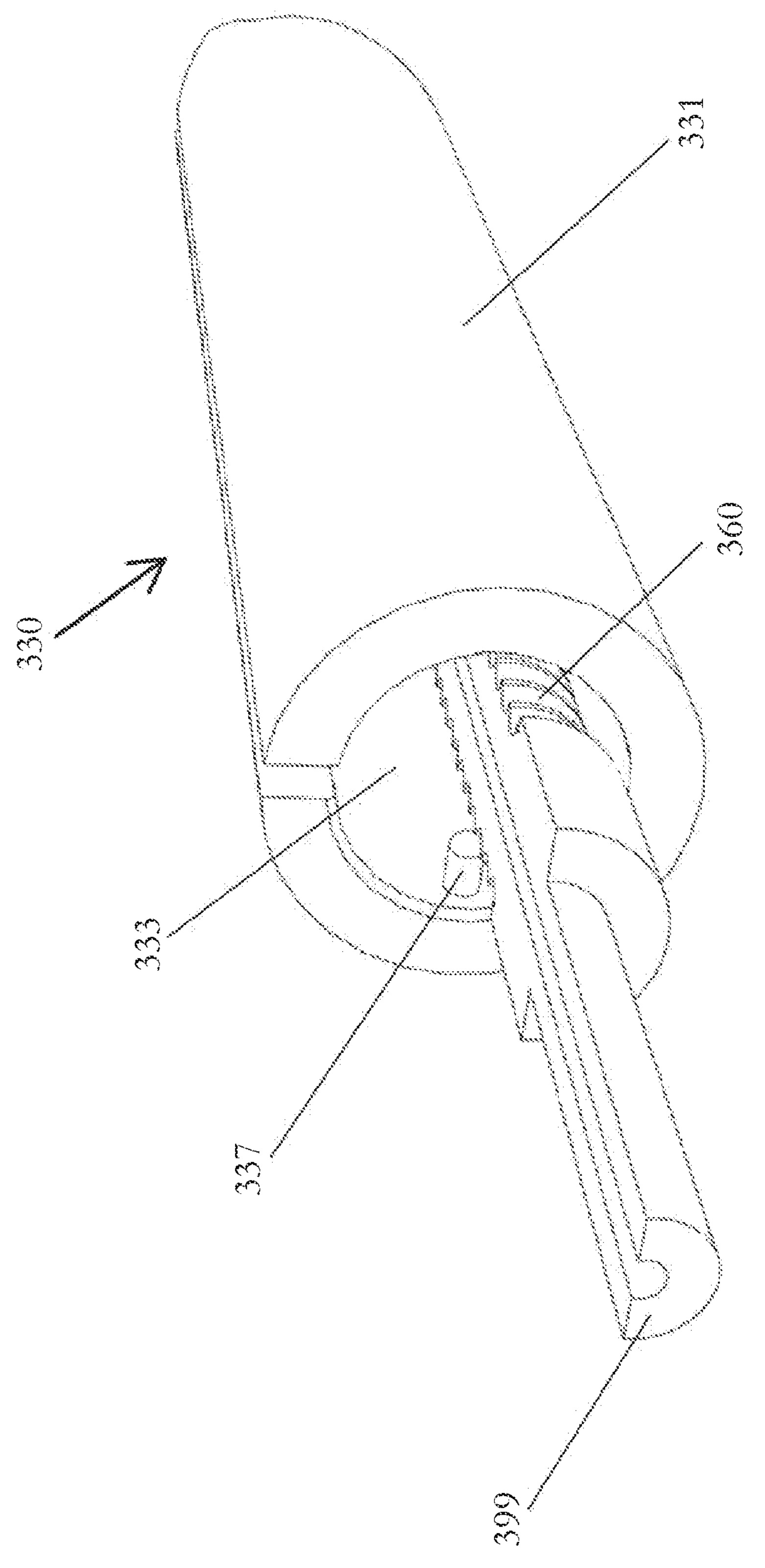

An alternative screw-path forming instrument receiving member 330 is shown in [FIG. 6*b*]. It has the same features as the screw-path forming instrument receiving member 30 shown in [FIG. 6*a*], such as the end cap 35 (not shown in [FIG. 6*b*]) and the ability to clamp the head of a connector between the inner member and the proximate end. However, in this alternative, instead of inner threads 34, a pin 337 is arranged protruding radially into the bore of the cylindrical body 331.

In use, the screw-path forming instrument 399 (shown only with the lower half-section to aid the clarity of the figure) may be inserted into the aperture 333 of the screw-path forming instrument receiving member 330. The instrument may then be rotated by hand such that the external screw threads 362 of the screw-path forming instrument 399 engage and cooperate with the pin 337. In this way, the screw thread forming means may be introduced in a controllable manner into the screw-path previously formed in the vertebra such that a screw thread is formed in the screw-path for subsequent insertion of a pedicle screw.

In [FIG. 7] a screw-path forming instrument 99 is shown. It comprises an elongate shaft 92 and a tap, or screw thread forming means 97, at one end. It also comprises an external screw thread portion 62, having a larger diameter than the shaft 92, approximately mid-way along the longitudinal length of the instrument. It also includes a guide tool mating section 98 between the external screw thread portion 62 and the screw thread forming means 97, in the form of a cylinder having a larger diameter than the shaft 92. It also comprises a collar 91, having a larger diameter than the shaft 92, at the end distal from the screw thread forming means 97.

In use, the screw-path forming instrument 99 may be inserted into the aperture 33 of the screw-path forming instrument receiving member 30. The guide tool mating section 98 will pass snugly through the screw-path forming instrument receiving section of the guide tool 60 such that the alignment of the instrument is controlled. The instrument may then be rotated by hand such that the external screw threads cooperate with the screw threads 34 provided on the bore of the screw-path forming instrument receiving member 30. In this way, the screw thread forming means 97 may be introduced in a controllable manner into the screw-path previously formed in the vertebra and create a screw thread in the screw-path for subsequent insertion of a pedicle screw. The screw-path may now be regarded as a screw-path.

The collar 91 prevents over-insertion of the instrument into the vertebra.

The instrument 99 and guide tool 60 may then be removed such that the guide tool stem is removed from the guide tool stem receiving section 24 in the pedicle screw 20 in the vertebra below the one in which the screw-path has just been formed.

In the alternative method depicted in [FIG. 6*a*], wherein the screw-path forming instrument receiving member 30 is attached to a connector 100, the instrument 99 and screw-path forming instrument receiving member 30 may then be removed such that the connector 100 remains in place with the connector stem 110 inserted in the connector stem receiving section 24 of the pedicle screw 20 in the vertebra below the one in which the screw-path has just been formed.

With regard to [FIG. 8], not only does the choice of guide tool 60 improve the positioning of the pedicle screw, but also the guide tool stem receiving section 24 in each pedicle screw 20 includes a guide tool stem receiving section which is a bore 24 through a ball-like portion 26 which fits between the arms of the guide tool stem receiving section 24 and is rotatable relative thereto as a ball and socket, or ball joint. In this way, with the guide tool stem 80 inserted into the guide tool stem receiving section 24, the guide tool 60 is moveable relative to the longitudinal axis of the threaded stem 22 of the pedicle screw 20. This movement is limited by the stem 80 abutting the arms of the guide tool stem receiving section 24 but still allows a considerable movement such that the screw-path forming instrument receiving section 70 of the guide tool may be positioned as required.

FIG. 9 shows the guide tool stem receiving section 24 in two different positions relative to the arms of the guide tool stem receiving section 24 to demonstrate this relative movement.

With the position and orientation of the screw-path forming instrument receiving section 70 selected by the choice of appropriate guide tool 60 and orientation of the ball-like portion 26 and thus the orientation of the guide tool relative to the longitudinal axis of the threaded stem 22 of the pedicle screw in the adjacent vertebra, the surgeon may now create a screw-path in the vertebra by means of the boring tool. In this regard, the ball-like portion 26 may be arranged not to move so freely within the arms of the guide tool stem receiving section 24 that the act of inserting the boring tool through the channel 70 moves the ball-like portion 26. However, it is sufficiently movable that it is movable by hand.

After removal of the guide tool stem from the connector stem receiving section 24 in the pedicle screw below, a connector stem 110 may then be inserted instead, into the connector stem receiving section 24. The connector 100 may be selected from a range of connectors, as shown in [FIG. 10]. These connectors 100 have identical, or very similar, geometries (length, angle of dependencies of the stems 110 from the head portions 120 etc.) as the range of guide tools 60. It is expected that the surgeon will select a connector having the same geometries as the guide tool 60 which was used to form the screw-path, however, this may not always be the case.

As shown in [FIG. 11], the head portion 120 of each connector 100 in the range includes a pedicle screw receiving section 130 which includes an aperture 135. The stem 110 is inserted into the connector stem receiving section 24, in the pedicle screw in the vertebra below the one in which the screw-path has just been formed. The aperture 135 is shown as a circular screw-path arranged to receive a pedicle screw, but other shapes are contemplated which allow the pedicle screw to fit through. The new pedicle screw 20 is therefore inserted through this aperture 135 and into the screw-path formed earlier.

As the connector 100 selected has the same geometries (shape, configuration, length, angle etc.) as the guide tool 60 which was used with the boring tool 90 to form the screw-path, it is expected that the new pedicle screw 20 will insert cleanly and relatively easily into the vertebra and lie at the chosen orientation relative to it.

The stem 110 of the connector 100 inserted into a connector stem receiving section 24, of a pedicle screw 20 is shown in [FIG. 12]. The stem 100 passes through the guide tool stem receiving section 24 (which now acts as a connector stem receiving section 24) which is arranged in the ball-like portion 26 which is arranged within the arms of the connector stem receiving section 24. However, it is to be understood that with the connector stem 110 of the connector 100 in place in the connector stem receiving section 24, and the new pedicle screw inserted through the pedicle screw receiving section 130 of the same connector 100, the ball joint will not move as freely as prior to the connector stem being inserted. [FIG. 14] shows a connector 100 with a pedicle screw 20 inserted through the aperture 135.

The method described above may be repeated for additional vertebrae, as required, such that several vertebrae each have a pedicle screw inserted and are connected together with connectors, as shown in [FIG. 1].

This spinal anchoring element system 5, may then be used to correct spinal deformities. This may be achieved by each connector 100 allowing movement of the pedicle screw 20 which passes through its pedicle screw receiving section 130 to move relative to its stem 110. This may be achieved by having the pedicle screw receiving section 130 arranged to pivot, or rotate, within arms 140 arranged either side of the head portion 120. In [FIG. 13] it can be seen that the pedicle screw receiving section 130 includes a projection 145 which has an arcuate surface and which corresponds to, and is slidable over, an arcuate surface 144 of the rear of the head portion 140 of the connector 100. These two opposing surfaces 144, 145 allow the pedicle screw receiving section 130 to move in a rotating manner about an axis which lies perpendicular to the longitudinal length of the stem 110 (i.e. the axis lies approximately parallel to the inter-section of the coronal and transverse planes). However, rather than allowing this movement to be uncontrolled, a ratchet 150 is arranged between at least one of the two outer, opposite, surfaces of the pedicle screw receiving section 130 and at least one of the inner surfaces of the arms 140 of the head portion 140. The ratchet 150 may be a series of ridges provided on each of these two surfaces.

Accordingly, in use, the ratchet may be arranged to allow two adjacent pedicle screws (each installed in an adjacent vertebra) to rotate about a common axis (approximately parallel to the inter-section of the coronal and transverse planes).

The ratchet 150 may allow the two pedicle screws to rotate about this common axis substantially only in opposite rotational directions so that over a period of time, and effected by active and passive movements of the spinal column during normal daily activities and exercising, gradual correction of a deformity of the spinal column may be achievable by substantially only permitting the anterior edges of the end plates of the two substantially adjacent vertebrae to move either closer to one another, or further apart from one another.

It will be noted that in [FIG. 11] a line 113 is shown extending along the stem 110 of the connector 100 from the head portion 120 to almost, but not quite, the extreme end of the stem distal from the head portion 120. This line indicates how the stem 110 and arms 140 of the head portion 120 are split into two portions such that they may be pulled slightly apart. This allows the pedicle screw receiving section 130 to be rotated within the arms 140 without the ratchet 150 engaging, and allows for the pedicle screw receiving section 130 to be oriented, as required, relative to the longitudinal length of the stem 110 prior to insertion of the stem 110 into the connector stem receiving section 24 of the pedicle screw installed in the adjacent vertebra.

The invention claimed is:

1. A spinal anchoring element system, comprising:

a) a screw-path forming instrument for use in forming a screw-path in a vertebra for the subsequent installation of a pedicle screw, b) a guide tool for aligning the screw-path forming instrument, wherein the guide tool comprises a guide tool stem and a screw-path forming instrument receiving section, the guide tool stem and the screw-path forming instrument receiving section being immovable relative to one another, and c) a screw-path forming instrument receiving member, the screw-path forming instrument receiving member including attachment means for attaching it to the guide tool, the screw-path forming instrument receiving member including an internal screw thread for receiving the screw-path forming instrument for creating a thread on the inside surface of the screw-path created in the vertebra by the screw-path forming instrument, wherein the screw-path forming instrument includes a guide tool mating section for aligning the screw-path forming instrument in relation to the guide tool.

2. The spinal anchoring element system according to claim 1, wherein the guide tool comprises substantially radiolucent material.

3. The spinal anchoring element system according to claim 1, wherein the screw-path forming instrument receiving section comprises a channel open at opposite axial ends, the channel having a bore, wherein the bore has a longitudinal axis.

4. The spinal anchoring element system according to claim 3, wherein the channel is defined by a cylindrical wall, the wall including a slot allowing, in use, a guide wire to be inserted into the channel.

5. The spinal anchoring element system according to claim 3, wherein the guide tool mating section has a size and shape which closely matches that of the bore of the channel so that the guide tool mating section is receivable, in use, into the bore of the channel to thereby align the screw-path forming instrument.

6. The screw-path forming instrument according to claim 5, wherein the guide tool mating section includes a depth limiter to limit axial movement, in one direction, of the screw-path forming instrument parallel to the longitudinal axis of the bore of the channel along said longitudinal axis, with the screw-path forming instrument received in the screw-path forming instrument receiving section.

7. The spinal anchoring element system according to claim 1, wherein the guide tool stem is arranged to fit, in use, into a guide tool stem receiving section of an adjacent pedicle screw.

8. The spinal anchoring element system according to claim 1, wherein the screw-path forming instrument includes an external screw thread, for reception in the screw-path forming instrument receiving member, and for creating the thread on the inside surface of the screw-path created in the vertebra by the screw-path forming instrument.

9. The spinal anchoring element system according to claim 1, further comprising a pedicle screw, the pedicle screw comprising a guide tool stem receiving section for receiving, in use, a second guide tool stem of a second guide tool.

10. The spinal anchoring element system according to claim 9, wherein the pedicle screw comprises a shaft having a screw thread, and the guide tool stem receiving section of the pedicle screw comprises a ball and socket joint for articulation of the guide tool stem relative to the shaft.

11. The spinal anchoring element system according to claim 9, further comprising a connector, the connector comprising a connector stem and a pedicle screw receiving section, the pedicle screw receiving section for receiving, in use, the guide tool stem receiving section of the pedicle screw.

12. The spinal anchoring element system according to claim 11, wherein the connector further comprises a ratchet for controlling movement of the pedicle screw receiving section relative to the connector stem.

13. The spinal anchoring element system according to claim 11, wherein the connector stem has a shape and size substantially the same as the guide tool stem.

* * * * *